US008003605B2

(12) United States Patent
Bayer et al.

(10) Patent No.: US 8,003,605 B2
(45) Date of Patent: Aug. 23, 2011

(54) MINIMISING BODY WEIGHT GAIN IN INSULIN TREATMENT

(75) Inventors: Thomas Bayer, Lyngby (DK); Signe Rikke Permild, legal representative, Lyngby (DK); Birgitte Sogaard, Gilleleje (DK); Mads Axelsen, Virum (DK)

(73) Assignee: Novo Nordisk A/S, Bagsvaerd (DK)

( * ) Notice: Subject to any disclaimer, the term of this patent is extended or adjusted under 35 U.S.C. 154(b) by 624 days.

(21) Appl. No.: 10/386,881

(22) Filed: Mar. 12, 2003

(65) Prior Publication Data

US 2003/0224973 A1 Dec. 4, 2003

Related U.S. Application Data

(60) Provisional application No. 60/366,327, filed on Mar. 14, 2002.

(30) Foreign Application Priority Data

Mar. 13, 2002 (DK) ............................ PA 2002 00395

(51) Int. Cl.
*A61K 38/28* (2006.01)
*C07K 14/62* (2006.01)
(52) U.S. Cl. ........................................................ 514/5.9
(58) Field of Classification Search ........................ None
See application file for complete search history.

(56) References Cited

U.S. PATENT DOCUMENTS

| 6,136,784 | A | * | 10/2000 | L'Italien et al. | 514/12 |
| 6,174,856 | B1 | * | 1/2001 | Langballe et al. | 514/4 |
| 6,451,970 | B1 | * | 9/2002 | Schaffer et al. | 530/303 |
| 2003/0171535 | A1 | * | 9/2003 | Schaffer et al. | 530/303 |
| 2003/0224973 | A1 | * | 12/2003 | Bayer et al. | 514/3 |

FOREIGN PATENT DOCUMENTS

WO WO 97/31022 * 8/1997

OTHER PUBLICATIONS

Definition of derivative. (http://www.answers.com/derivative&r=67) accessed online Nov. 10, 2005. 1 page.*
Rudinger. In: Peptide Hormones, JA Parsons, Ed. (1976) pp. 1-7.*
Sigma: Designing Custom Peptides, http://www.sigma-genosys.com/peptide_design.asp (accessed online Dec. 16, 2004) 2 pages.*
Berendsen. A Glimpse of the Holy Grail? Science (1998) vol. 282, pp. 642-643.*
Voet et al. Biochemistry, 2nd edition (1995) pp. 235-241.*
Smilek et al. A single amino acid change in a myelin basic protein oeptide confers the capacity to prevent rather than induce experimental autoimmune encephalomyelitis. PNAS USA. 1991, vol. 88, pp. 9633-9637.*
Messer. Vasopressin and Oxytocin, web document updated Apr. 3, 2000, http://www.neurosci.pharm.utoledo.edu/MBV3320/vasopressin.htm, 5 pages.*
Axelsen et al. More Predictable Fasting Blood Glucose with the New Soluble Basal Insulin Analogue, Insulin Detemir: A Comparison with NPH in Type I Diabetes Patients. Diabetes Research and Clinical Practice. Sep. 2000, vol. 50, No. Suppl. 1, p. S79.*
Brunner et al. Pharmacokinetic and pharmacodynamic properties of long-acting insulin analogue NN304 in comparison to NPH insulin in humans. Exp Clin Endocrinal Diabetes 2000, 108, pp. 100-105.*
Calculate your BMI—Standard BMI Calculator at http://www.nhlbisuppport.com/bmi accessed online Aug. 15, 2006.*
Standl. Insulin Analogues—State of the Art. Hormone Res 2002; 57 (suppl 1) pp. 40-45.*
Simpson et al. Insulin aspart. Drugs May 1999, vol. 57, No. 5, pp. 759-765.*
White. The Pharmacological Reduction of Blood Glucose in Patients With Type 2 Diabetes Mellitus. Clinical Diabetes, 1998, vol. 12, No. 2, pp. 58-67.*
Bognetti et al. Prevalence and correlates of obesity in insulin dependent diabetic patients. Archives of Disease in Childhood. 1995. vol. 73, pp. 239-242.*
Detournay et al. Diabetes and Metabolism. Managing type 2 diabetes in France: the ECODIA survey. 2000. vol. 26, No. 5, pp. 1-19.*
Kraine et al. The Role of Environmental Factors in Insulin-Dependent Diabetes Mellitus: An Unresolved Issue. Environmental Health. 1999. vol. 107, Supplement 5., pp. 777-781.*
Levemir® insulin detemir (rDNA origin) injection. Novo Norkisk. Date of Issue: May 16, 2007, pp. 1-2.*
Atkinson et al. Type 1 diabetes: new perspectives on disease pathogenesis and treatment. The Lancet. vol. 358, Jul. 21, 2001, pp. 221-229.*
Influence of Intensive Diabetes Treatment on Body Weight and Composition of Adults With Type 1 Diabetes in the Diabetes Control and Complications Trial, Diabetes Care, vol. 24, No. 10, pp. 1711-1721, Oct. 2001.
Memorandum Opinion (*Sanofi-Aventis v. Novo Nordisk Inc.*, Civil Action No. 06-1369.
Memorandum Of Novo Nordisk Inc., In Opposition To Plaintiff's Motion For a Preliminary Injunction, Apr. 7, 2006.
Declaration of Alan C. Moses, M.D, dated Apr. 6, 2006.
Declaration of Brian Blakey, dated Apr. 5, 2006.
Declaration of Lene Andersen, dated Apr. 5, 2006.
Declaration of Wayne Pines, dated Apr. 5, 2006.
Sanofi-Aventis' Complaint against Novo Nordisk; Mar. 23, 2006.
Declaration of John E. Timberlake, dated Mar. 22, 2006. Declaration of John E. Gerich, M.D., dated Mar. 22, 2006.
Kurtzhals et al, Diabetes, 2000, vol. 49, No. 6, pp. 999-1005.
Vague et al., Diabetes Care, 2003, vol. 26, No. 3, pp. 590-596.
Standl et al., 38th Annual Meeting of EASD, 1 Sep. 1, 2002, Budapest, Hungary, XP002243151.
Slee, PR Newswire: Immedia.IT/Puglished/20010910/2001091016194, "Study Shows Insulin Detemir Controls Blood Glucose Levels More Predictably", 2001, XP002243152.

* cited by examiner

*Primary Examiner* — Marcela M Cordero Garcia
(74) *Attorney, Agent, or Firm* — Michael J. Brignati

(57) ABSTRACT

A method for minimizing weight gain, preventing weight gain or inducing weight loss in a mammal, said method involving a treatment regimen which comprises administration of an insulin derivative having a substituent containing from 6 to 40 carbon atoms attached to one of its amino acid residues.

13 Claims, No Drawings

MINIMISING BODY WEIGHT GAIN IN INSULIN TREATMENT

CROSS-REFERENCE TO RELATED APPLICATIONS

This application claims priority under 35 U.S.C. of Danish application no. PA 2002 00395 filed Mar. 13, 2002, and U.S. application No. 60/366,327 filed Mar. 14, 2002, the contents of which are fully incorporated herein by reference.

FIELD OF THE INVENTION

This invention relates to a method for minimising weight gain in the treatment of diabetes mellitus, either type 1 diabetes or type 2 diabetes and conditions associated with diabetes mellitus.

BACKGROUND OF THE INVENTION

For several years it has been known that when treatment of diabetic patients with insulin is initiated the body weight of the patients generally starts to increase (see, for example, the results of the Diabetes Control and Complications Trial (DCCT) Research Group: Influence of Intensive Diabetes Treatment on Body Weight and Composition of Adults With Type 1 Diabetes in the Diabetes Control and Complications Trial. Diabetes Care 24:1711-1721, 2001). The body weight continues to increase for many years after the intensive insulin treatment is initiated. The problem is most pronounced in intensive insulin treatment but also known with conventional treatment. Since intensive insulin treatment significantly reduces the risk of development and progression of late complications such as retinopathy, nephropathy, and neuropathy compared with conventional therapy, intensive diabetes therapy is much preferred over conventional therapy. The major adverse effect of intensive treatment is an increase in severe hypoglycemia. After the increased rate of hypoglycemia, weight gain and increased risk of obesity are the most evident side effects of intensive treatment.

SUMMARY OF THE INVENTION

The present invention provides a method for minimising weight gain or preventing weight gain in a mammal, said method involving a treatment regimen which comprises administration of an insulin derivative having a substituent containing from 6 to 40 carbon atoms attached to one of its amino acid residues, in the following also referred to as a lipophilic insulin or an insulin derivative.

In one embodiment of the invention, the mammal is a human type 1 diabetic patient.

In another embodiment of the invention, the mammal is a human type 1 diabetic patient undergoing conventional insulin treatment.

In another embodiment of the invention, the mammal is a human type 1 diabetic patient undergoing intensive insulin treatment.

In another embodiment of the invention, the mammal is a human type 2 diabetic patient undergoing conventional insulin treatment.

In another embodiment of the invention, the mammal is a human type 2 diabetic patient undergoing intensive insulin treatment.

In another embodiment of the invention, the mammal is a human type 1 diabetic patient having a BMI (Body Mass Index) in the range 20-35 kg/m$^2$, preferably 20-27 kg/m$^2$.

In another embodiment of the invention, the mammal is a human type 2 diabetic patient.

In another embodiment of the invention, the mammal is a human type 2 diabetic patient having a BMI (Body Mass Index) in the range 20-52 kg/m$^2$, preferably 27-45 kg/m$^2$.

In another embodiment of the invention, the human diabetic patient is treated with a lipophilic insulin having a substituent containing from 6 to 40 carbon atoms attached to one of its amino acid residues. Such lipophilic insulins are disclosed in U.S. Pat. Nos. 5,750,497, 6,001,007, WO 96/29344, U.S. Pat. No. 5,693,609, and U.S. Pat. No. 5,922,675 all of which are incorporated herein by reference. The lipophilic insulin may be provided in the form of a zinc complex which binds 1, 2, 3, or 4 zinc ions per insulin hexamer.

In another embodiment of the invention, the human diabetic patient is treated with a lipophilic insulin having a substituent which is an acyl group having from 6 to 40 carbon atoms, more preferred from 6 to 30 carbon atoms, still more preferred from 6 to 20 carbon atoms.

In another embodiment of the invention, the human diabetic patient is treated with a lipophilic insulin having a substituent which is an acyl group having 8 carbon atoms.

In another embodiment of the invention, the human diabetic patient is treated with a lipophilic insulin having a substituent which is an acyl group having from 14 carbon atoms.

In another embodiment of the invention, the human diabetic patient is treated with a lipophilic insulin having a substituent which is an acyl group having from 21 carbon atoms.

In another embodiment of the invention, the human diabetic patient is treated with a lipophilic insulin having a substituent which is an acyl group having from 29 carbon atoms.

In another embodiment of the invention, the human diabetic patient is treated with a lipophilic insulin having a substituent which is an acyl group forming an amide in combination with the epsilon-amino group of a Lys residue present in the parent insulin.

In another embodiment of the invention, the human diabetic patient is treated with a lipophilic insulin which is insulin detemir.

In another embodiment of the invention, the human diabetic patient is treated with a lipophilic insulin which is $N^{\epsilon B29}$-(lithocholoyl-γ-Glu) des(B30) human insulin.

In another embodiment of the invention, the human diabetic patient is treated with a lipophilic insulin which is NE$^{\epsilon B29}$-octanoyl human insulin.

In another embodiment of the invention, the human diabetic patient is treated with an anti-diabetic agent further to the lipophilic insulin.

In another embodiment of the invention, the human diabetic patient is treated with a rapid-acting insulin further to the lipophilic insulin.

In another embodiment of the invention, the human diabetic patient is treated with human insulin further to the lipophilic insulin.

In another embodiment of the invention, the human diabetic patient is treated with insulin aspart further to the lipophilic insulin.

In another embodiment of the invention, the human diabetic patient is treated with insulin lispro further to the lipophilic insulin.

In another embodiment of the invention, the human diabetic patient is treated with Lys$^{B3}$Glu$^{B29}$ human insulin further to the lipophilic insulin.

In another embodiment of the invention, the human diabetic patient is treated with GLP-1 further to the lipophilic insulin.

In another embodiment of the invention, the human diabetic patient is treated with a GLP-1 analogue further to the lipophilic insulin.

In another embodiment of the invention, the human diabetic patient is treated with a derivative of a GLP-1 analogue further to the lipophilic insulin.

In another embodiment of the invention, the human diabetic patient is treated with an α-glucosidase inhibitor further to the lipophilic insulin.

In another embodiment of the invention, the human diabetic patient is treated with an insulin secretagogue further to the lipophilic insulin.

In another embodiment of the invention, the human diabetic patient is treated with glibenclamide further to the lipophilic insulin.

In another embodiment of the invention, the human diabetic patient is treated with glipizide further to the lipophilic insulin.

In another embodiment of the invention, the human diabetic patient is treated with gliclazide further to the lipophilic insulin.

In another embodiment of the invention, the human diabetic patient is treated with glimepiride further to the lipophilic insulin.

In another embodiment of the invention, the human diabetic patient is treated with tolazamide further to the lipophilic insulin.

In another embodiment of the invention, the human diabetic patient is treated with tolbutamide further to the lipophilic insulin.

In another embodiment of the invention, the human diabetic patient is treated with acetohexamide further to the lipophilic insulin.

In another embodiment of the invention, the human diabetic patient is treated with carbutamide further to the lipophilic insulin.

In another embodiment of the invention, the human diabetic patient is treated with chlorproxamide further to the lipophilic insulin.

In another embodiment of the invention, the human diabetic patient is treated with glibornuride further to the lipophilic insulin.

In another embodiment of the invention, the human diabetic patient is treated with gliquidone further to the lipophilic insulin.

In another embodiment of the invention, the human diabetic patient is treated with glisentide further to the lipophilic insulin.

In another embodiment of the invention, the human diabetic patient is treated with glosolamide further to the lipophilic insulin.

In another embodiment of the invention, the human diabetic patient is treated with glisoxepide further to the lipophilic insulin.

In another embodiment of the invention, the human diabetic patient is treated with glyclopyramide further to the lipophilic insulin.

In another embodiment of the invention, the human diabetic patient is treated with glycyclamide further to the lipophilic insulin.

In another embodiment of the invention, the human diabetic patient is treated with repaglinide further to the lipophilic insulin.

In another embodiment of the invention, the human diabetic patient is treated with nateglinide further to the lipophilic insulin.

In another embodiment of the invention, the human diabetic patient is treated with an insulin sensitizer further to the lipophilic insulin.

In another embodiment of the invention, the human diabetic patient is treated with an insulin sensitizer which is a thiazolidine-2,4-dione derivative further to the lipophilic insulin.

In another embodiment of the invention, the human diabetic patient is treated with ciglitazone further to the lipophilic insulin.

In another embodiment of the invention, the human diabetic patient is treated with rosiglitazone further to the lipophilic insulin.

In another embodiment of the invention, the human diabetic patient is treated with pioglitazone further to the lipophilic insulin.

In another embodiment of the invention, the human diabetic patient is treated with englitazone further to the lipophilic insulin.

In another embodiment of the invention, the human diabetic patient is treated with troglitazone further to the lipophilic insulin.

In another embodiment of the invention, the human diabetic patient is treated with metformin further to the lipophilic insulin.

In another embodiment of the invention, the human diabetic patient is treated with 3-[4-[2-(phenoxazin-10-yl)ethoxy]phenyl]-2-ethoxypropanoic acid or a salts thereof, e.g. NN622 further to the lipophilic insulin.

In a further aspect of the invention, treatment of human diabetic patients with a lipophilic insulin leads to a reduced number of nocturnal hypoglycaemic episodes. This reduction in the number of nocturnal hypoglycaemic episodes can amount to 15% reduction, 25% reduction or even 35% reduction of the number that could otherwise have been expected.

In a further aspect of the invention, treatment of human diabetic patients with a lipophilic insulin leads to a much reduced day to day variation in the fasting plasma glucose level and in the fasting blood glucose level.

In a still further aspect, the invention relates to a method for preventing increase in the body weight of overweight diabetic patients, said method involving a treatment regimen which comprises administration of an insulin derivative having a substituent containing from 6 to 40 carbon atoms attached to one of its amino acid residues.

In another particular embodiment of the present invention, insulin detemir is used in combination with insulin aspart. Use of this combination ensures that the patient's body weight gain—if any—will be very moderate. Also, the combined use of insulin detemir and insulin aspart will result in a statistically significant, clinically relevant, very favourable lowering of the $HbA_{1c}$ level of the patients. Furthermore, a very low day to day variation in the fasting plasma glucose level and in the fasting blood glucose level will be seen and the number of nocturnal hypoglycaemic episodes will be low compared to what is seen with conventional therapy.

Definitions

In the following, certain terms used in the present text are defined:

"Conventional insulin therapy" or "conventional insulin treatment" means insulin therapy comprising 1-2 injections per day with mixtures of rapid-, intermediate-, or long-acting insulin.

"Intensive insulin therapy" or "intensive insulin treatment" means either an insulin therapy that comprises continuous subcutaneous infusion or several daily insulin injections, typically 1-4, 1-3 or 1-2 injections per day with a basal (long-acting) insulin, supplemented with injections of human insulin or a rapid-acting analogue e.g. in connection with meals with frequent blood glucose testing. The regimen comprising the combined use of a long-acting insulin and human insulin or a rapid-acting analogue is also designated a basal/bolus regimen.

"Insulins having a lipophilic substituent" or "lipophilic insulins" means natural insulins or insulin analogues that have a lipophilic substituent attached which makes the substituted product more lipophilic than the parent insulin.

"Insulin analogue" means human insulin which has been modified by having one or more amino acid residues deleted and/or exchanged and/or by having one or more amino acid residues added at the N-terminal and/or the C-terminal of the A-chain and/or the B-chain and which has insulin activity.

"Insulin detemir" is the International Non-proprietary Name for $N^{\epsilon B29}$-tetradecanoyl des(B30) human insulin.

DESCRIPTION OF THE INVENTION

Examples of insulins having a lipophilic substituent which are useful in the insulin therapy according to the present invention are $N^{\epsilon B29}$-acylated derivatives of human insulin and des(B30) human insulin, $N^{\epsilon B28}$-acylated derivatives of insulin analogues having Lys at position B28 and $N^{\epsilon B3}$-acylated derivatives of insulin analogues having Lys at position B3, for example:

$N^{\epsilon B29}$-tetradecanoyl des(B30) human insulin;
$N^{\epsilon B29}$-(lithocholoyl-γ-Glu) des(B30) human insulin;
$N^{\epsilon B28}$-tetradecanoyl $Lys^{B28}Pro^{B29}$ human insulin;
$N^{\epsilon B29}$-tetradecanoyl $Asp^{B28}$ human insulin;

Examples of insulin secretagogues useful in an insulin therapy according to the present invention are: glibenclamide, glipizide, gliclazide, glimepiride, tolazamide, tolbutamide, acetohexamide, carbutamide, chlorproxamide, glibornuride, gliquidone, glisentide, glosolamide, glisoxepide, glyclopyamide, glycyclamide, repaglinide and nateglinide.

Examples of insulin sensitizers useful in an insulin therapy according to the present invention are: thiazolidine-2,4-diones such as ciglitazone, pioglitazone, rosiglitazone, englitazone, troglitazone and 3-[4-[2-(phenoxazin-10-yl)ethoxy]phenyl]-2-ethoxypropanoic acid and salts thereof, e.g. NN622.

Pharmaceutical Compositions

The insulin compositions used according to the present invention may be administered parenterally to patients in need of such a treatment. Parenteral administration may be performed by subcutaneous, intramuscular or intravenous injection by means of a syringe, optionally a pen-like syringe. Alternatively, parenteral administration can be performed by means of an infusion pump. A further option is a composition which may be a powder or a liquid for the administration of the human insulin derivative in the form of a nasal or pulmonary spray.

The insulin compositions may be prepared by conventional techniques, e.g. as described in *Remington: The Science and Practise of Pharmacy*, 19$^{th}$ Ed., 1995.

Thus, injectable insulin compositions can be prepared using the conventional techniques of the pharmaceutical industry which involves dissolving and mixing the ingredients as appropriate to give the desired end product.

Thus, according to one procedure, the desired insulin or insulin derivative is dissolved in an amount of water which is somewhat less than the final volume of the composition to be prepared. An isotonic agent, a preservative, a buffer and if needed a zinc salt or other metal salt is added as required and the pH value of the solution is adjusted—if necessary—using an acid, e.g. hydrochloric acid, or a base, e.g. aqueous sodium hydroxide as needed. Finally, the volume of the solution is adjusted with water to give the desired concentration of the ingredients.

Examples of isotonic agents are sodium chloride, mannitol, sorbitol, glycerol, propylene glycol and dimethyl sulfone.

Examples of preservatives are phenol, m-cresol, methyl p-hydroxybenzoate and benzyl alcohol.

Examples of suitable buffers are sodium acetate and sodium phosphate.

Pharmaceutical compositions of the lipophilic insulins used in the present invention are solutions containing hexameric complexes. Typically the hexameric complexes are stabilized by two or more zinc ions and three or more molecules of a phenolic compound like phenol or metacresol or mixtures thereof per hexamer.

In a particular embodiment, a composition is provided which contains two different insulins, one having a protracted profile of action and one having a rapid onset of action, in the form of soluble hexameric complexes. Typically the hexameric complexes are stabilized by two or more zinc ions and three or more molecules of a phenolic compound like phenol or metacresol or mixtures thereof per hexamer. The complexes are mixtures of hexamers of the particular insulins and mixed hexamers in which the ratio between the two different insulins is in the range from 1:10 to 10:1, for example from 1:5 to 5:1.

A composition for nasal administration of an insulin may, for example, be prepared as described in European Patent No. 272097 (to Novo Nordisk A/S).

Crystals for pulmonal administration of an insulin may, for example, be prepared as described in U.S. Pat. No. 6,310,038 (to Novo Nordisk A/S).

Aqueous solutions for pulmonal administration of an insulin may, for example, be prepared as described in WO 00/23098, WO 00/23099 or WO 00/29013 (all to Novo Nordisk A/S).

The optimal dose level for any patient will depend on a variety of factors including the efficacy of the specific insulin derivative and other anti-diabetic agent employed, the age, the body weight, the physical activity, and the diet of the patient, on a possible combination with other drugs, and on the severity of the case of diabetes. It is recommended that the daily dosage of the medicaments used in the regimen according to this invention be determined for each individual patient by those skilled in the art.

EXAMPLES

The present invention is further illustrated by the following examples which, however, are not to be construed as limiting the scope of protection.

Example 1

Section a): A 6-month multi-centre, open-label, randomised, parallel trial comparing efficacy and safety of the basal insulin analogue insulin detemir and NPH insulin in patients with type 1 diabetes on a basal (twice daily)-bolus regimen and Section b): A 6-month extension trial.
Section a):

Background and Aims: The efficacy and safety of insulin detemir was compared to NPH in a 6-month, multi-centre, multi-national, open, randomised, parallel trial in type 1 diabetic patients on a basal (twice daily)-bolus regimen with human soluble insulin as bolus insulin. One of the secondary objectives of the study was to compare the regimens in terms of the safety profile, including the body weight of the patients.

Material and Methods: A total of 460 patients with no clinically significant diseases or diabetic complications were exposed (287 men and 173 women).

Results: Mean (SD) age: 39.2 (12.9) years; mean duration of diabetes: 14.7 (10.0) years; mean BMI: 25.3 (3.3) kg/M$^2$; mean HbA$_{1c}$: 7.6 (1.2)%. 421 (91.5%) patients completed the trial (insulin detemir: 212; NPH: 209). Insulin detemir provided similar glycaemic control when compared to NPH, as measured by HbA$_{1c}$, 9-point blood glucose profiles and fasting plasma glucose (FPG) after 6 months of treatment. HbA$_{1c}$ was comparable for insulin detemir and NPH with an absolute mean difference between treatments (insulin detemir-NPH) of 0.08% point and a 95% CI of [−0.05; 0.22]. No statistically significant difference in FPG was found between treatments (p=0.78), and the 9-point blood glucose profiles for insulin detemir and NPH were comparable. There was a tendency towards lower intra-patient variation in fasting blood glucose (FBG) for insulin detemir indicating more predictable FBG levels (not statistically significant, p=0.06). The safety profiles were comparable between the two treatments, with no safety concerns. The number of patients with hypoglycaemic episodes was not statistically significantly different between the two treatments.

Results Regarding the Body Weight of the Patients
ANOVA of weight (kg) after 6 months of treatment, ITT Only patients contributing to the analysis, i.e. for whom both baseline and end of trial value are available are included in this table Conclusions Regarding the Body Weight of the Patients On average, the patients in the insulin detemir group lost 0.5 kg during the trial while patients in the NPH insulin group gained 0.7 kg.

Section b). 6-Month extension trial:

Background and aims: This trial compared the safety and efficacy of insulin detemir and NPH insulin in adult patients with type 1 diabetes. The trial was a multi-centre, multinational, open-label, parallel-group, 6-month extension study of a 6-month randomized, comparative study of insulin detemir and NPH insulin. All patients were on a basal (twice-daily)-bolus regimen with human soluble insulin as meal related insulin:

Materials and methods: 288 patients were exposed to trial medication in the extension trial (154 on insulin detemir and 134 on NPH insulin; 184 males and 104 females; mean (SD) age: 41.6 (12.9) years). A total of 252 patients (134 on insulin detemir, 118 on NPH insulin) completed the 12 month treatment period. Similar glycemic control as measured by HbA$_{1c}$, 9-point blood glucose profiles and fasting plasma glucose was observed in the two treatment groups after 12 months of treatment.

Results: HbA$_{1c}$ values of 7.9% and 7.8% were found for insulin detemir and NPH insulin, respectively. Insulin detemir showed a trend towards lower risk of hypoglycemia during the night (relative risk (detemir/NPH)=0.71, p=0.067).

The proportion of patients with serious adverse events during 12 months was lower in the insulin detemir group (9.1% versus 13.4%). In conclusion, insulin detemir and NPH insulin provided similar glycemic control and comparable safety profiles after 1 year of treatment.

Results Regarding the Body Weight of the Patients
ANOVA of weight (kg) after 12 months of treatment, ITT

| Insulin detemir | | | NPH insulin | | | insulin detemir − NPH | | |
|---|---|---|---|---|---|---|---|---|
| N | Mean | (SE) | N | Mean | (SE) | Mean | 95% CI | p-value |
| 211 | 75.4 | (0.27) | 209 | 76.5 | (0.27) | −1.16 | [−1.71, −0.60] | <0.001 |

The analysis is based upon an ANOVA model with treatment and country as fixed effects and weight at baseline as covariate.

Mean: Least square mean, SE: Standard error of the mean, CI: Confidence interval Summary of body weight (kg) at Baseline and End of Trial

| Insulin detemir | | | | | | NPH insulin | | | | | |
|---|---|---|---|---|---|---|---|---|---|---|---|
| Baseline | | | End of trial | | | Baseline | | | End of trial | | |
| N | Mean | (SD) | N | Mean | (SD) | N | Mean | (SD) | N | Mean | (SD) |
| 209 | 76.5 | (12.6) | 209 | 76.1 | (13.2) | 206 | 75.6 | (12.7) | 206 | 76.3 | (12.9) |

| Insulin detemir | | | NPH insulin | | | Insulin detemir − NPH | | |
|---|---|---|---|---|---|---|---|---|
| N | Mean | (SE) | N | Mean | (SE) | Mean | 95% CI | p-value |
| 133 | 75.2 | (0.47) | 118 | 76.9 | (0.50) | −1.66 | [−2.68, −0.63] | 0.002 |

The analysis is based upon an ANOVA model with treatment and country as fixed effects and weight at baseline as covariate.

Mean: Least square mean, SE: Standard error of the mean, CI: Confidence interval.

Summary of body weight (kg) at Baseline and End of Trial

| Insulin detemir Baseline | | | End of trial | | | NPH insulin Baseline | | | End of trial | | |
|---|---|---|---|---|---|---|---|---|---|---|---|
| N | Mean | (SD) | N | Mean | (SD) | N | Mean | (SD) | N | Mean | (SD) |
| 132 | 76.6 | (12.2) | 132 | 76.3 | (13.0) | 118 | 75.8 | (13.4) | 118 | 77.2 | (13.8) |

Only patients contributing to the analysis, i.e. for whom both baseline and end of trial value are available are included in this table.

Conclusion Regarding the Body Weight of the Patients

A weight loss (not statistically significant) of 0.3 kg was observed in the insulin detemir group, while a statistically significant 1.4 kg weight gain was observed in the NPH insulin group, resulting in a significant and clinically relevant difference between groups after 12 months of treatment (1.7 kg, p=0.002).

Example 2

Section a): A six month multi-centre, open-label, randomised, parallel trial comparing efficacy and safety of the basal insulin analogue insulin detemir and NPH insulin in patients with type 1 diabetes on a basal (twice daily)-bolus regimen with insulin aspart as bolus insulin.

Section b): A 6-month extension trial.

Section a):

Background and aims: This trial compared the glycemic control, risk of hypoglycemia and effect on body weight of insulin detemir and NPH insulin in type 1 diabetic patients treated with the rapid-acting insulin analogue insulin aspart at meals. One of the secondary objectives of the study was to compare the regimens in terms of the safety profile, including the body weight of the patients.

Materials and methods: This was a 6-month, multinational, open, parallel-group comparison conducted at 46 centres in five countries, including 448 type 1 diabetic patients randomized 2:1 to insulin detemir or NPH insulin, respectively.

Results: After 6 months, comparable HbA, levels were found between the two treatment groups (insulin detemir: 7.60%, NPH insulin: 7.64%). Fasting plasma glucose tended to be lower in patients treated with insulin detemir, but this difference was not statistically significant (−0.76 mM, p=0.097). Within-patient variation in self-measured fasting blood glucose was lower with insulin detemir than with NPH insulin (SD=3.37 vs 3.78 mM, p<0.001). Overall risk of hypoglycemia was 22% (95% CI [3-38%], p<0.05) lower and nocturnal hypoglycemia 34% (95% CI [13-50%], p<0.005) lower with insulin detemir compared to NPH insulin. The shapes of the nightly plasma glucose profiles were significantly different between the two treatments, being smoother and more stable with insulin detemir (p=0.05) with lower plasma glucose at 07:00 (7.6 mM/L vs 9.5 mM/L, p<0.05). Body weight (baseline adjusted) was significantly lower with insulin detemir at the end of the trial (p<0.001). In conclusion, treatment with insulin detemir resulted in more predictable glycemic control with smoother plasma glucose profiles than NPH insulin, and a significant reduction in the risk of hypoglycemia, especially during the night. The observed reduction in body weight with insulin detemir is an additional advantage. The general safety profile was similar between the two treatments.

Results Regarding the Body Weight of the Patients

ANOVA of weight (kg) after 6 months of treatment, ITT

| Insulin detemir | | | NPH insulin | | | insulin detemir − NPH | | |
|---|---|---|---|---|---|---|---|---|
| N | Mean | (SE) | N | Mean | (SE) | Mean | 95% CI | p-value |
| 282 | 70.9 | (0.28) | 138 | 71.8 | (0.33) | −0.98 | [−1.55, −0.41] | 0.001 |

The analysis is based upon an ANOVA model with treatment as fixed effect and weight at baseline as covariate.

Mean: Least square mean, SE: Standard error of the mean, CI: Confidence interval Summary of body weight (kg) at Baseline and End of Trial

| Insulin detemir Baseline | | | End of trial | | | NPH insulin Baseline | | | End of trial | | |
|---|---|---|---|---|---|---|---|---|---|---|---|
| N | Mean | (SD) | N | Mean | (SD) | N | Mean | (SD) | N | Mean | (SD) |
| 278 | 71.5 | (11.8) | 278 | 71.2 | (12.2) | 136 | 71.0 | (11.4) | 136 | 71.7 | (11.9) |

Only patients contributing to the analysis, i.e. for whom both baseline and end of trial value are available are included in this table.

Conclusion Regarding the Body Weight of the Patients

On average, patients in the insulin detemir group lost 0.2 kg (not statistically significant) over 6 months, while patients in the NPH insulin group gained 0.7 kg. All together, the result was a statistically significant difference in mean body weight between the groups of 1 kg.

Section b), 6-Month extension trial:

Title: An extension trial comparing long-term safety of the basal insulin analogue insulin detemir and NPH insulin in patients with type 1 diabetes on a basal (twice daily)-bolus regimen. A 6-month extension of a multi-centre, open-label, asymmetrically randomised, parallel trial.

Objectives

One of the secondary objectives of the study was to compare the regimens in terms of the safety profile, including the body weight of the patients.

Methodology

The trial was a 6-month extension of a multi-centre, multinational, open-label, comparative, asymmetrically (2:1), randomised (insulin detemir: NPH insulin) parallel group trial comparing efficacy and safety of insulin detemir and NPH insulin in patients with type 1 diabetes who had been on a basal (twice daily)-bolus regimen with IAsp as meal related insulin.

Patients who agreed to participate in the extension period continued treatment without interruption.

Following completion of the 6-month initial period, the extension period included 3 visits (0, 3 and 6 months after the start of the extension period).

Patients continued in the extension period on the treatment they were receiving in the first 6-month period (insulin detemir+IAsp or NPH insulin+IAsp). The patients were advised to maintain their usual diet and daily activities.

Patients

All patients who completed the 6-month treatment period in the trial described under Section a) above and who were able and willing to participate in the extension period were included. Thus, the Section b) trial included 316 patients.

Results Regarding the Body Weight of the Patients

ANOVA of weight (kg) after 12 months of treatment, ITT

| Insulin detemir | | | NPH insulin | | | insulin detemir − NPH | | |
|---|---|---|---|---|---|---|---|---|
| N | Mean | (SE) | N | Mean | (SE) | Mean | 95% CI | p-value |
| 211 | 71.5 | (0.34) | 96 | 72.8 | (0.42) | −1.34 | [−2.12, −0.56] | 0.001 |

The analysis is based upon an ANOVA model with treatment as fixed effect and weight at baseline as covariate.

Mean: Least square mean, SE: Standard error of the mean, CI: Confidence interval Summary of body weight (kg) at Baseline and End of Trial

| Insulin detemir Baseline | | | End of trial | | | NPH insulin Baseline | | | End of trial | | |
|---|---|---|---|---|---|---|---|---|---|---|---|
| N | Mean | (SD) | N | Mean | (SD) | N | Mean | (SD) | N | Mean | (SD) |
| 209 | 71.4 | (10.8) | 209 | 71.3 | (11.4) | 96 | 71.5 | (12.5) | 96 | 72.7 | (13.1) |

Only patients contributing to the analysis, i.e. for whom both baseline and end of trial value are available are included in this table.

Conclusion Regarding the Body Weight of the Patients

On average, patients in the insulin detemir group lost 0.1 kg (not statistically significant) during the trial while patients in the NPH insulin group gained 1.2 kg resulting in a statistically significant and clinically relevant difference between the groups after 12 months of 1.3 kg.

Example 3

A 6-month, multi-centre, open-label, parallel efficacy and safety comparison of insulin detemir and NPH insulin in patients with type 1 diabetes on a basal/bolus regimen.

Objectives

One of the secondary objectives of the study was to compare the regimens in terms of the safety profile, including the body weight of the patients.

Methodology

This was a 6-month, multinational, open-label, randomised, parallel group trial comparing once daily treatment with insulin detemir to NPH insulin in patients with type 1 diabetes. All patients were on a basal/bolus insulin regimen with human soluble insulin as meal-related insulin. A 2:1 randomisation (insulin detemir: NPH insulin) was used. The trial included a screening visit to assess patient eligibility and a randomisation visit (maximum 3 weeks after the screening visit) followed by a six-month treatment period. In order to achieve glycaemic control, the investigator had contact with the patients at least every other working day during the first two weeks of treatment or as long as necessary to achieve glycaemic control. A post-treatment follow-up visit was performed 2-6 days after the last visit.

Patients

The study included 750 type 1 diabetic patients aged 18 years or above and having a $HbA_{1c} \leq 12\%$. The patients had a history of diabetes of at least 1 year and had been on a basal (once daily between 17:00 and 23:00)—bolus insulin treatment $\geq 2$ months with a total daily dose below 100 IU/day, of which basal insulin requirement $\geq 30\%$. The patients were to have no major diabetic complications or other significant diseases.

Results Regarding the Body Weight of the Patients

ANOVA of weight (kg) after 6 months of treatment, ITT

| Insulin detemir | | | NPH insulin | | | insulin detemir − NPH | | |
|---|---|---|---|---|---|---|---|---|
| N | Mean | (SE) | N | Mean | (SE) | Mean | 95% CI | p-value |
| 463 | 76.2 | (0.15) | 234 | 76.7 | (0.20) | −0.52 | [−0.97, −0.07] | 0.024 |

The analysis is based upon an ANOVA model with treatment and country as fixed effects and weight at baseline as covariate.

Mean: Least square mean, SE: Standard error of the mean, CI: Confidence interval Summary of body weight (kg) at Baseline and End of Trial

| Insulin detemir Baseline | | | End of trial | | | NPH insulin Baseline | | | End of trial | | |
|---|---|---|---|---|---|---|---|---|---|---|---|
| N | Mean | (SD) | N | Mean | (SD) | N | Mean | (SD) | N | Mean | (SD) |
| 460 | 76.5 | (12.3) | 460 | 76.3 | (12.4) | 234 | 76.1 | (12.5) | 234 | 76.5 | (12.6) |

Only patients contributing to the analysis, i.e. for whom both baseline and end of trial value are available are included in this table.

Conclusion Regarding the Body Weight of the Patients

On average, patients in the insulin detemir group lost 0.2 kg during the trial, while patients in the NPH insulin group gained 0.4 kg.

Example 4

A 6-month, multi-centre, open, asymmetrically randomised, parallel, efficacy and safety comparison of insulin detemir and NPH insulin in patients with type 2 diabetes on a basal/bolus regimen.

Objectives

One of the secondary objectives of the study was to compare the regimens in terms of the safety profile, including the body weight of the patients.

Methodology

Multicentre, open, randomised, parallel trial comprising a screening visit and a randomisation visit followed by a six month treatment period of basal/bolus therapy with either insulin detemir or NPH once or twice daily as needed. The patients received NovoRapid® with meals as bolus insulin throughout the trial.

Patients

The study included 506 type 2 diabetic patients aged 35 years or above with type 2 diabetes for $\geq 12$ months treated with insulin or insulin analogues for at least 2 months, with a $HbA_{1c} \leq 12.0\%$, a basal insulin dose $\geq 30\%$ of the total daily insulin dose and no other clinically relevant diseases were included in the trial.

Results Regarding the Body Weight of the Patients

ANOVA of weight (kg) after 6 months of treatment, ITT

| Insulin detemir | | | NPH insulin | | | insulin detemir – NPH | | |
|---|---|---|---|---|---|---|---|---|
| N | Mean | (SE) | N | Mean | (SE) | Mean | 95% CI | p-value |
| 314 | 87.8 | (0.28) | 156 | 88.6 | (0.33) | −0.79 | [−1.44, −0.14] | 0.017 |

The analysis is based upon an ANOVA model with treatment and country as fixed effects and weight at baseline as covariate.

Mean: Least square mean, SE: Standard error of the mean, CI: Confidence interval Summary of body weight (kg) at Baseline and End of Trial

| Insulin detemir Baseline | | | End of trial | | | NPH insulin Baseline | | | End of trial | | |
|---|---|---|---|---|---|---|---|---|---|---|---|
| N | Mean | (SD) | N | Mean | (SD) | N | Mean | (SD) | N | Mean | (SD) |
| 314 | 85.4 | (14.8) | 314 | 85.8 | (15.1) | 155 | 89.7 | (17.6) | 155 | 91.0 | (18.5) |

Only patients contributing to the analysis, i.e. for whom both baseline and end of trial value are available are included in this table.

Conclusion Regarding the Body Weight of the Patients

The mean body weight in the insulin detemir group increased significantly less than in the NPH insulin group (0.4 kg versus 1.3 kg).

Example 5

Administration of insulin detemir morning and pre-dinner or insulin detemir morning and bedtime or NPH insulin morning and bedtime in patients with type 1 diabetes Objectives One of the secondary objectives of the study was to compare the three regimens in terms of the safety profile, including the body weight of the patients.

Methodology

This was a 16-week multinational, open-label, randomised (1:1:1), parallel, three arm clinical trial, comparing the efficacy and safety of insulin detemir administered morning and pre-dinner, insulin detemir administered morning and bedtime, and NPH insulin administered morning and bedtime in patients with type 1 diabetes. All patients received insulin aspart (IAsp) with meals. The trial included a Screening Visit to assess patient eligibility and a Randomisation Visit (maximum 2 weeks after the Screening Visit). The following 16 week treatment period included 5 visits. In addition, patients were contacted every second day in the first two weeks (or longer if necessary) to ensure that optimal basal insulin dose was achieved fast and smoothly. A post-treatment telephone Follow-up was performed approximately one week after the last visit.

Patients

The study included 400 type 1 diabetic patients aged 18 or above with a BMI of $\leq 35$ m$^2$/kg and $HbA_{1c} < 12\%$. The patients had had diabetes $\geq 12$ months and had been treated on a basal/bolus regimen $\geq 2$ months with a basal insulin requirement of $\geq 30\%$ of the total daily insulin dose, and a total daily basal insulin dose below 100 IU. Patients were to have no major diabetic complications or other significant diseases.

Results Regarding the Body Weight of the Patients

ANOVA of Weight (kg) after 16 Weeks of Treatment—Adjusted for Change in $HbA_{1c}$, ITT

| Overall Test | N | Mean | (SE) | P-value |
|---|---|---|---|---|
| Detemir Morn_Dinner | 132 | 75.12 | (0.22) | |
| NPH Morn_Bed | 122 | 76.40 | (0.22) | |
| Detemir Morn_Bed | 121 | 75.81 | (0.22) | |
| | | | | <0.0001 |
| Pairwise Comparisons | Mean Difference | | 95% CI | P-value |
| Detemir Morn_Dinner – NPH Morn_Bed | −1.3 | | (−1.9, −0.7) | <0.0001 |
| Detemir Morn_Bed – NPH Morn_Bed | −0.6 | | (−1.2, 0.0) | 0.0504 |
| Detemir Morn_Dinner – Detemir Morn_Bed | −0.7 | | (−1.3, −0.1) | 0.0182 |

The analysis is based upon an ANOVA model with treatment, country and $HbA_{1c}$ change from baseline as fixed effects and weight at baseline as covariate Mean: Least square mean, SE: Standard Error of the mean, CI: Confidence interval Summary of body weight (kg) at Baseline and End of Trial

| Insulin detemir Baseline | | | End of trial | | | NPH insulin Baseline | | | End of trial | | |
|---|---|---|---|---|---|---|---|---|---|---|---|
| N | Mean | (SD) | N | Mean | (SD) | N | Mean | (SD) | N | Mean | (SD) |
| 253 | 76.3 | (14.4) | 253 | 76.2 | (14.8) | 122 | 74.5 | (13.2) | 122 | 75.3 | (13.7) |

Only patients contributing to the analysis, i.e. for whom both baseline and end of trial value are available are included in this table.

Conclusion Regarding the Body Weight of the Patients

Weight was lower in both insulin detemir groups compared with NPH insulin; this difference was statistically significant.

Example 6

A 16 week, multi-centre, multi-national, open, randomised three-group parallel study comparing administration of insulin detemir at 12-hour intervals, insulin detemir morning and bedtime and NPH morning and bedtime in patients with type 1 diabetes Objectives One of the secondary objectives of the study was to compare the three regimens in terms of the safety profile, including the body weight of the patients.

Methodology

The trial was a multi-centre, multi-national, open-label, 1:1:1 randomised, three arm parallel group clinical trial of 16 weeks of treatment comparing the efficacy and safety of insulin detemir administered at 12-hour intervals, insulin detemir administrated morning and bedtime and NPH insulin administered morning and bedtime in patients with type 1 diabetes. All patients received insulin aspart at meals. The trial included a Screening Visit to assess patient's eligibility and a Randomisation Visit, followed by a treatment period 16 of weeks. A post-treatment follow-up Visit was carried out approximately 1 week after the last visit.

Patients

The study included 409 type 1 diabetic patients aged 18 or above and $HbA_{1c} \leq 12\%$. The patients had had diabetes >12 months and had been treated on a basal (twice daily)/bolus regimen $\geq 2$ months using an intermediate/long-acting insulin as a basal insulin and fast-acting human insulin or insulin analogue as bolus insulin.

Results Regarding the Body Weight of the Patients

ANOVA of Weight (kg) after 16 Weeks of Treatment—Adjusted for Change in $HbA_{1c}$, ITT

| Overall Test | N | Mean | (SE) | P-value |
|---|---|---|---|---|
| Detemir 12 h_interval | 131 | 75.20 | (0.22) | |
| NPH Morn_Bed | 122 | 76.04 | (0.23) | |
| Detemir Morn_Bed | 132 | 75.41 | (0.22) | |
| | | | | 0.0180 |

| Pairwise Comparisons | Mean Diff. | 95% CI | P-value |
|---|---|---|---|
| Detemir 12 h_interval − NPH Morn_Bed | −0.8 | (−1.4, −0.24) | 0.0061 |
| Detemir Morn_Bed − NPH Morn_Bed | −0.6 | (−1.2, −0.03) | 0.0397 |
| Detemir 12 h_interval − NPH Morn_Bed | −0.2 | (−0.80, 0.37) | 0.4772 |

The analysis is based upon an ANOVA model with treatment and country and change $HbA_{1c}$ as fixed effects and weight at baseline as covariate.

Mean: Least square mean, SE: Standard Error of the mean, CI: Confidence interval Summary of body weight (kg) at Baseline and End of Trial

| Insulin detemir Baseline | | | End of trial | | | NPH insulin Baseline | | | End of trial | | |
|---|---|---|---|---|---|---|---|---|---|---|---|
| N | Mean | (SD) | N | Mean | (SD) | N | Mean | (SD) | N | Mean | (SD) |
| 263 | 76.3 | (12.3) | 263 | 76.2 | (12.3) | 122 | 74.5 | (14.3) | 122 | 75.3 | (14.6) |

Only patients contributing to the analysis, i.e. for whom both baseline and end of trial value are available are included in this table.

Conclusion Regarding the Body Weight of the Patients

On the average, patients in the Detemir 12 h_interval group maintained their weight, whereas patients in the Detemir Morn_Bed group gained 0.2 kg and patients in the NPH Morn_Bed group gained 0.7 kg.

Example 7

An 18 week, multi-centre, multinational, open-labelled, randomised, parallel-group comparison of insulin detemir plus insulin aspart with NPH insulin plus human soluble insulin in patients with type 1 diabetes on a basal-bolus regimen Objectives The primary objective of the trial was:

To compare the glycaemic control, measured by $HbA_{1c}$, of insulin detemir administered twice daily plus mealtime insulin aspart with that of NPH insulin administered twice daily plus mealtime human soluble insulin in patients with type 1 diabetes on a basal/bolus regimen.

The secondary objectives was to compare the effect of insulin detemir administered twice daily plus mealtime insulin aspart with that of NPH insulin administered twice daily plus mealtime human soluble insulin in terms of:

The intra-patient variation in home measurements of blood glucose.

Glucose control as assessed by the 8-point blood glucose profiles.

Glucose control as assessed with interstitial glucose sensor profiles (subgroup of patients).

The incidence of self-recorded hypoglycaemic episodes (minor, major and symptomatic) overall, daytime and nighttime.

The safety profile by occurrence of adverse events during the trial period The safety profile as measured by laboratory safety parameters (haematology, biochemistry and lipids), physical examination and body weight measurements before and at the end of treatment and vital signs during the trial period.

Methodology

The trial was a multi-centre, multinational, open-labelled, symmetrically randomised (1:1), parallel group trial comparing insulin detemir plus insulin aspart with NPH insulin plus human soluble insulin in patients with type 1 diabetes. The patients received basal insulin (insulin detemir or NPH insulin) twice daily (in the morning and at bedtime) and bolus insulin (insulin aspart or human soluble insulin) prior to meals.

The trial included a screening visit to assess the eligibility of the patients and a randomisation visit maximum 2 weeks after the screening visit, followed by a titration period of 6 weeks and a 12-week maintenance period.

Patients

The study included a total of 595 type 1 diabetic patients (males and females) aged 18 or above with a BMI of ≦35 kg/m² and $HbA_{1c}$≦12%. The patients had had diabetes≧12 months. Current treatment with any basal/bolus regimen or any biphasic insulin treatment for at least 6 months.

Patients with proliferative retinopathy or maculopathy requiring acute treatment, recurrent major hypoglycaemia, anticipated change in concomitant medication known to interfere with glucose metabolism, impaired hepatic or renal function, cardiac problems, uncontrolled hypertension and/or a total daily insulin dose ≧1.4 IU/kg, are excluded from the trial.

Summary of body weight (kg) at Baseline and End of Trial

| Insulin detemir + insulin aspart | | | | NPH insulin + human soluble insulin | | | |
|---|---|---|---|---|---|---|---|
| Baseline | | End of trial | | Baseline | | End of trial | |
| N | Mean | N | Mean | N | Mean | N | Mean |
| 298 | 73.6 | 298 | 72.8 | 297 | 74.4 | 297 | 74.5 |

Only patients contributing to the analysis, i.e. for whom both baseline and end of trial value are available are included in this table.

The invention claimed is:

1. A method for minimizing weight gain in a diabetic patient, said method comprising administering to said diabetic patient in need of such treatment a first agent which is $N^{\epsilon B29}$-tetradecanoyl des(B30) human insulin in an amount effective to minimize said weight gain, and wherein the administering is a daily administration of said first agent for a period of more than 6 months, wherein the amount of weight gain during the period of administration is less than the amount of weight gain in comparison to the administration of an equivalent amount of NPH insulin, and wherein the diabetic patient is a type 2 diabetic patient having a body mass index (BMI) in the range of 20-52 kg/m².

2. The method according to claim 1, wherein said method further comprises administering a second agent selected from the group consisting of human insulin, a rapid-acting analogue thereof, an insulin secretagogue, and an insulin sensitizer.

3. The method according to claim 2, wherein the second agent is likely to cause weight gain when used alone.

4. The method according to claim 1, wherein said administering of $N^{\epsilon B29}$-tetradecanoyl des(B30) human insulin is performed at least once daily.

5. The method according to claim 4, wherein said administering is once or twice daily.

6. The method according to claim 1, wherein the $N^{\epsilon B29}$-tetradecanoyl des(B30) human insulin is administered by infusion via an insulin pump.

7. The method according to claim 1, wherein the administration is once daily for a period of more than 12 months.

8. The method according to claim 1, wherein the administering is an intensive insulin treatment comprising basal/bolus treatment.

9. The method according to claim 8, comprising administering the insulin derivative $N^{\epsilon B29}$-tetradecanoyl des(B30) human insulin at least once per day and administering bolus insulin 2 to 6 times per day.

10. The method according to claim 8, comprising administering the insulin derivative $N^{\epsilon B29}$-tetradecanoyl des(B30) human insulin twice daily and administering bolus insulin 3 to 6 times daily.

11. The method according to claim 2, wherein the first agent is insulin detemir and the second agent is insulin aspart.

12. The method according to claim 1, wherein the type 2 diabetic patient having a BMI in a range of 27-45 kg/m$^2$.

13. A method for minimizing weight gain in a diabetic patient, said method comprising administering to said diabetic patient in need of such treatment a first agent which is N$^{\epsilon B29}$-tetradecanoyl des(B30) human insulin in an amount effective to minimize said weight gain, and wherein the administering is a daily administration of said first agent for a period of more than 6 months, wherein the amount of weight gain during the period of administration is less than the amount of weight gain in comparison to the administration of an equivalent amount of NPH insulin, and wherein the diabetic patient is a type 1 diabetic patient having a body mass index (BMI) in the range of 20-27 kg/m$^2$.

* * * * *